United States Patent [19]
Iacob

[11] Patent Number: 5,643,210
[45] Date of Patent: Jul. 1, 1997

[54] ANGIOPLASTY PERFUSION CATHETER

[76] Inventor: Mihai Iacob, Clinic of Cardiology, Fundeni Hospital, Sos. Fundeni 258, Sect. 2, RO - Bucharest, Romania

[21] Appl. No.: 671,260

[22] Filed: Jun. 26, 1996

Related U.S. Application Data

[63] Continuation of Ser. No. 245,027, May 17, 1994, abandoned.

[30] Foreign Application Priority Data

Jun. 23, 1993 [EP] European Pat. Off. .............. 93110022

[51] Int. Cl.⁶ ......................................... A61M 29/00
[52] U.S. Cl. ..................... 604/102; 604/96; 606/191; 606/192; 606/194
[58] Field of Search ..................... 604/93, 96, 95, 604/97, 98, 99, 101, 102, 103, 104; 606/191, 192, 194, 195

[56] References Cited

U.S. PATENT DOCUMENTS

| | | | |
|---|---|---|---|
| 4,892,519 | 1/1990 | Songer et al. ........................... | 604/96 |
| 4,983,167 | 1/1991 | Sahota ..................................... | 604/96 |
| 5,024,658 | 6/1991 | Kozlov et al. . | |
| 5,046,503 | 9/1991 | Schneiderman . | |
| 5,108,370 | 4/1992 | Walinsky ................................. | 604/96 |
| 5,137,513 | 8/1992 | McInnes et al. . | |
| 5,181,911 | 1/1993 | Shturman . | |
| 5,284,473 | 2/1994 | Calabria ................................. | 606/192 |
| 5,370,617 | 12/1994 | Sahota ..................................... | 606/194 |
| 5,378,237 | 1/1995 | Boussignac et al. ..................... | 604/96 |

*Primary Examiner*—Robert A. Hafer
*Assistant Examiner*—N. Kent Gring
*Attorney, Agent, or Firm*—Anthony J. Casella; Gerald E. Hespos

[57] ABSTRACT

The catheter comprises a perfusion catheter, a balloon connected by its distal end to a conduit and by its proximal end to an inflating tube, a guide wire inside the conduit, a dilator member in the perfusion catheter around the conduit and with a tapered front portion, and side orifices in the walls of the perfusion catheter and of the conduit before the balloon to allow blood flow. Upon usage, only the guide wire and conduit dragging the deflated balloon are inserted into the stenosis, the balloon is then inflated a short while to break the stenosis and thereafter deflated to permit insertion of the perfusion catheter therein by means of the dilator member; the dilator member and guide wire are then withdrawn and the balloon is re-inflated for supporting the vessel wall.

13 Claims, 2 Drawing Sheets

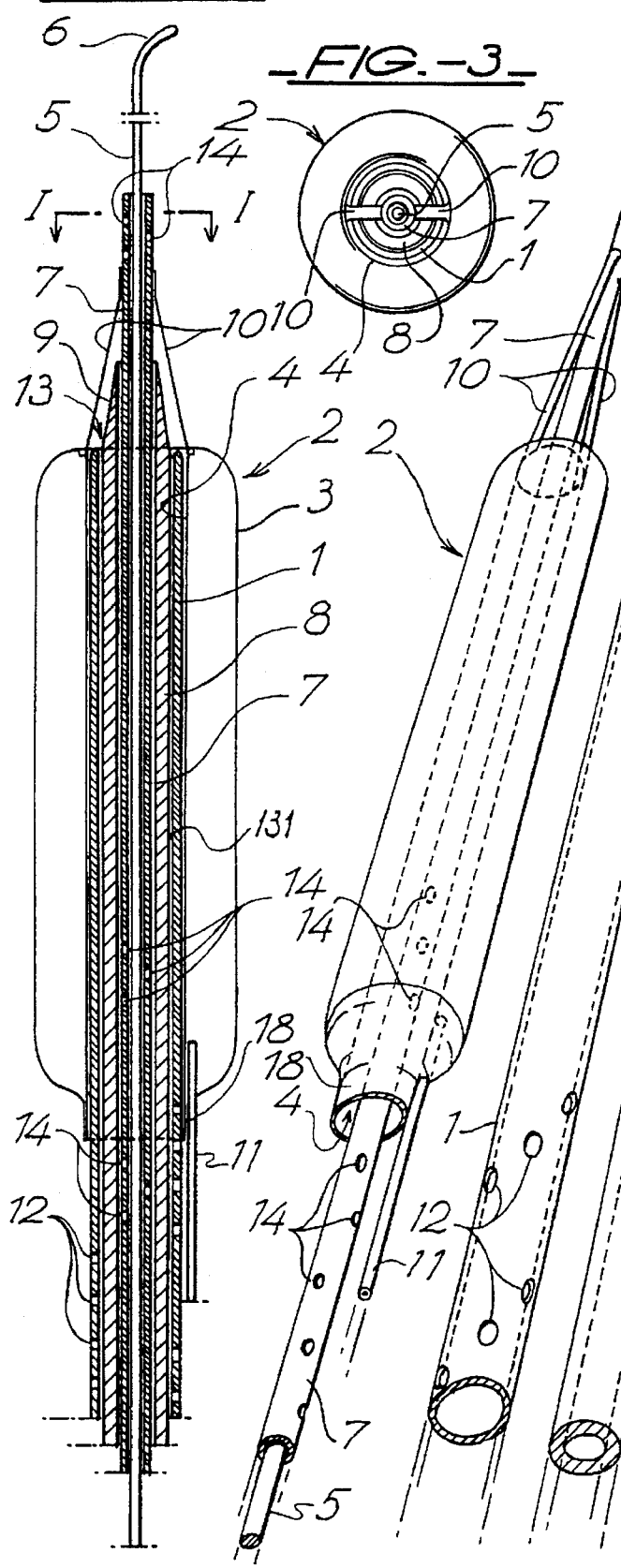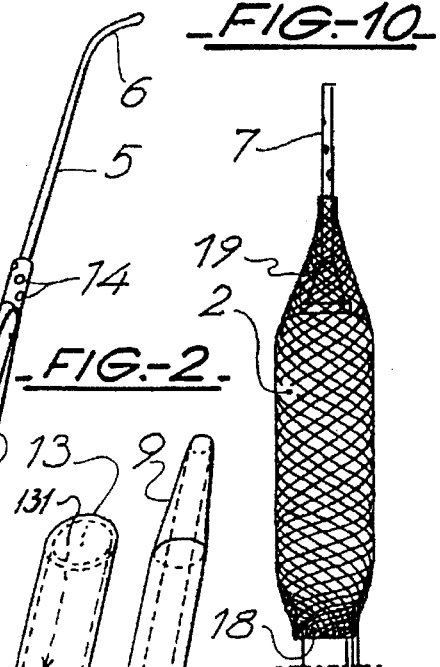

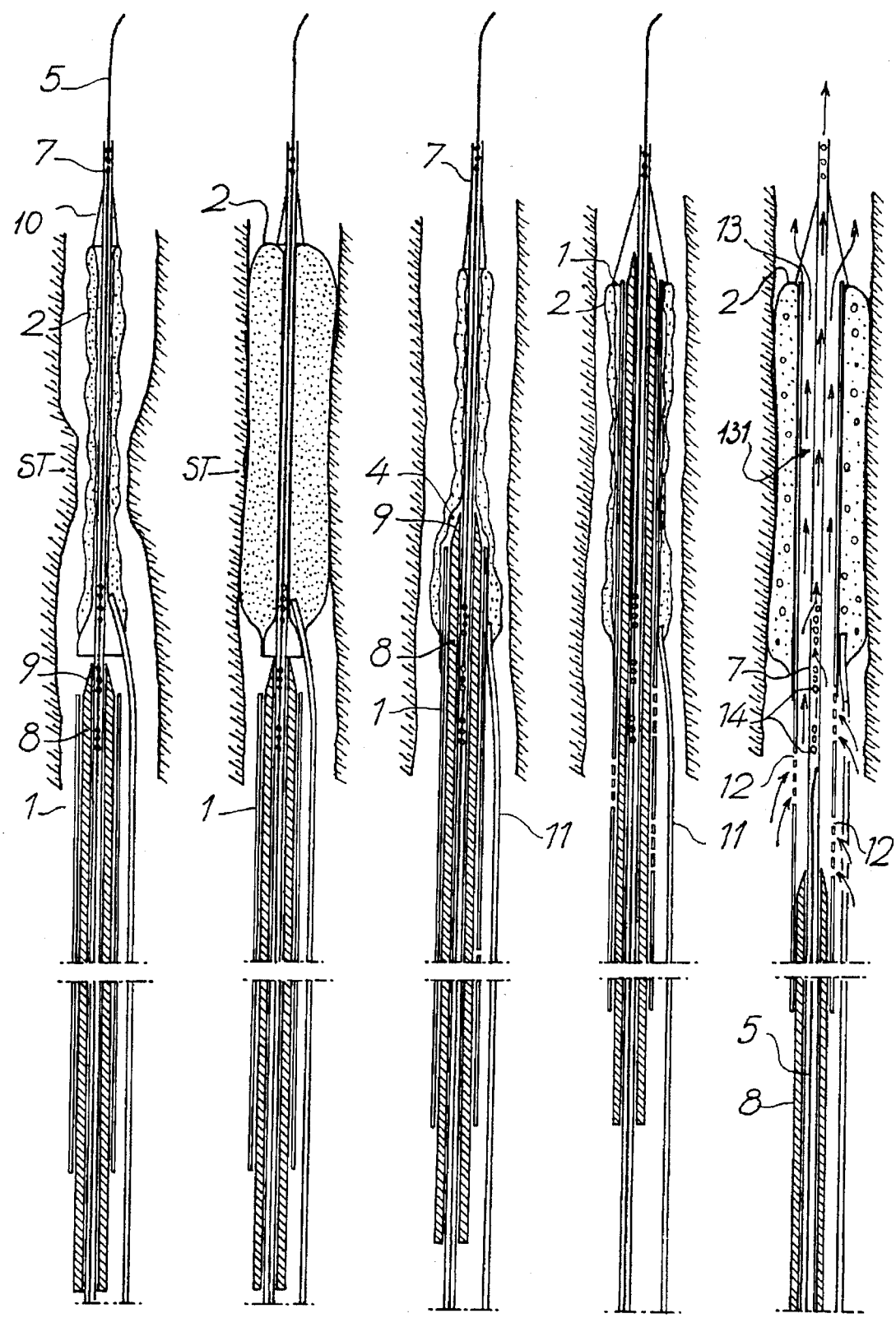

ANGIOPLASTY PERFUSION CATHETER

This application is a continuation of application Ser. No. 08/245,027 filed May 17, 1994 which application is now abandoned.

BACKGROUND OF THE INVENTION

This invention relates to angioplasty perfusion catheters with a perfusion channel, comprising a dilatation balloon and a perfusion tunnel through the balloon.

Catheters of that kind, such as the perfusion catheter described in U.S. Pat. No. 4,581,017, permit the insertion of the depressurized balloon into a stenosis; the balloon may then by expanded by means of a suitable fluid supply feeding the inflating tube in order to compress the stenosis radially outward; as the perfusion catheter has a side orifice located before the balloon, the blood may flow through the perfusion catheter past the balloon and the stenosis to exit through a central outlet at the distal end of the perfusion catheter, which maintains continuity of blood flow in the blood vessel, and which obviates the necessity of removing the catheter from a stenotic artery every five-ten seconds in order to avoid heart damage due to lack of blood flow. Inflation times longer than five-ten seconds become necessary when, due to the dilatation by the balloon, flaps have been formed in the vessel, and these flaps threaten to obstruct the vessel. Therefore, the dilatation balloon must be inflated repeatedly in the position of the stenosis in order to support the flaps and press them back to the vessel wall where they heal and bind again to the vessel wall. Sometimes, this process is finished in a very short time; but often, this favourable short healing is still too long to allow complete cutting of the blood flow during that time. That is the occasion where perfusion balloon catheters are needed because they allow extension of the inflation time without endangering blood supply to the heart muscles.

In order to be inserted into narrow stenosis the depressurized balloon must be capable of reduction to a minimal thickness around the perfusion catheter; it must also be capable to withstand the high inflating pressures which are required for angioplasty. Hence, the balloon must have walls which are as thin as possible to assure a low profile when depressurized and which are as strong as possible to withstand high pressure.

According to the aforesaid U.S. Pat. No. 4,581,017 the perfusion catheter runs axially through the balloon which is annularly fastened to the catheter by its fore and rear ends. In that environment, the perfusion catheter must be sufficiently stiff to constitute sort of an inner support wall for the balloon to prevent collapse thereof upon inflation in order to give way to the blood flow from beginning to end of the balloon as from the side orifice of the perfusion catheter up to the central outlet thereof. Specifically, it must be sufficiently stiff to withstand the high inflating pressures which are required for angioplasty. However, if the tube has a sufficient diameter to be effective as a perfusion channel, then this requirement results in a considerable wall thickness for the inner catheter, so that the overall minimum diameter of the catheter is increased unfavourably for its use as an interventional instrument for action in narrow stenosis. At the same time, the rigidity of the catheter is increased by this wall thickness of the tube, and it becomes then difficult to place the catheter in tortuous vessels.

As an alternative for the passage of the blood flow through the perfusion catheter during inflation of the balloon, another embodiment provides for having a balloon connected to the outer surface of a tube, the wall of the balloon comprising a pair of longitudinal lobes with portions between the lobes being formed to have thicker walls than the lobes whereby inflation of the balloon causes the lobes to expand radially outward to compress the stenosis while the thicker portions are expected to remain in close proximity to the exterior surface of the tube and provide way for the blood flow past the balloon. In a further alternative for the passage of the blood flow during inflation of the balloon, the balloon is also connected to the outer surface of a tube and is made of a plurality of segments or lobes angularly spaced from each other to allow blood flow upon inflation of the system. In each of these alternatives, if a segmented or lobed balloon fails to achieve the desired result when inflated in a particular angular orientation in the blood vessel, it is necessary to deflate the balloon or balloons, rotate the catheter, and then reinflate the balloon or balloons to complete widening of the stenosis.

Further, when the tubes are designed to be connected to the outer surface of the tube, then it is difficult to accommodate the necessary space for the safe welding or gluing on the surface of a small diameter inner tube.

These problems do not come up with the balloon catheter structures shown in U.S. Pat. Nos. 4,909,252, 5,002,531 and 5,108,370. In these documents, the dilatation balloons have an inflated shape which is toroidal with an elongated longitudinal central aperture or tunnel adapted to allow blood flow during dilatation of the balloon against the stenosis. These balloons are affixed to a catheter by at least one of their walls and the catheter passes inside, or outside, or through the balloon. In the balloons of U.S. Pat. Nos. 4,909,252 and 5,002,531, the inner wall forming the tunnel for blood flow is connected to the outer wall by welding areas or by junction struts regularly spaced apart from each other to avoid deformation of the balloon upon inflation and the resulting reduction of the central tunnel for the blood flow. These areas of junction to the catheter as well as the welding points and junction struts are difficult to manufacture and also constitute solutions of continuity which will generate peak stresses upon inflation of the balloon. The welding points and junction struts also add to the diametral space occupied by the balloon when depressurized. Specifically, the welding points and junction struts have to be sized sufficiently to take up the full inflation pressure required for angioplasty. In absence of such welding points or junction struts as shown in U.S. Pat. No. 5,108,370, the perfusion tunnel through the balloon will collapse under the inflation pressure required for angioplasty, even if the balloon is designed to be relatively short.

In other words, there is a choice of having an internal solid structure inside the balloon to keep the perfusion channel open. This choice sets limits to the diameter of the perfusion channel because the perfusion channel in this case directly determines the minimum deflated diameter of the balloon. Or there is another choice of having a foldable perfusion tunnel that collapses during deflation. This alternative makes struts or similar supporting structures inside the balloon necessary, which are difficult to manufacture, which create peak stresses in the balloon wall and which even when these problems were solved, still would add unfavourably to the diametral space occupied by the balloon when depressurized.

The object of this invention is to seek a substantial reduction of the diametral space occupied by the balloon of an angioplasty perfusion catheter when depressurized for its introduction into a stenosis of a blood vessel, while still providing a large sized perfusion channel for effective blood exchange through the balloon.

To this effect, the angioplasty perfusion catheter according to the invention complies with the definitions given in the claims.

Accordingly, the movable perfusion catheter defining the perfusion channel allows substantial reduction of the diametral space occupied by the balloon of an angioplasty perfusion catheter when depressurized for its introduction into a stenosis of a blood vessel while still allowing a large sized perfusion channel for effective blood exchange through the balloon, because it permits removal of the space consuming perfusion catheter out of the balloon when the latter is deflated. The free flying conduit for the guide wire in the perfusion tunnel allows collapse of the balloon without inducing the guidewire movement but still allows free access to the perfusion tunnel for tubular supporting members guided on the conduit, such as a perfusion catheter. This causes substantial diameter reduction of the depressurized catheter while the perfusion channel size can be increased and selected independently from the size of the depressurized catheter. And a free flying conduit in the perfusion catheter allows passage of a tubular dilator member guided on the conduit to open up the perfusion tunnel for insertion of a perfusion catheter that is considerably larger in size than the conduit.

In that way, the operator may initially only insert into the stenosis the guide wire and its tubular conduit dragging the deflated balloon, while leaving the perfusion catheter in waiting position behind the stenosis, whereby the diametral space occupied by the balloon is minimal for entry into narrow stenosis. As a second step, the operator inflates the balloon in the stenosis for a very short while sufficient to enlarge the stenosis, and immediately thereafter he deflates the balloon to reinstate blood flow through the stenosis. As a third step following deflation of the balloon, the operator may slide the perfusion catheter along the tubular conduit of the guide wire in order to make way into the perfusion tunnel of the deflated balloon. Then, as a fourth step, the operator inflates the balloon to support the vessel wall as long as necessary, the blood flow being assured through the perfusion catheter.

Accordingly, two process phases will be considered, namely:

a first angioplasty phase in which the amount of available pressure to the balloon is of primary importance to break the stenosis, the time during which the pressure is applied being of secondary importance;

a second support phase during which vessel wall flaps that may have been created by the dilatation are secured to the vessel wall; during this phase, time is determining not pressure, because there is no need to have high pressure to put the flaps back to the vessel wall from which they came loose, but there is needed some time until those flaps will connect again to the vessel wall.

In accordance with the invention, this two phase procedure is achieved with a single instrument allowing free diameter choice for the perfusion catheter to ensure good perfusion effect with high volume flow and least risk of blood clogging in narrow channels. The benefit of low pressure in the perfusion phase is then that even when large perfusion diameters are employed, the wall thickness of the perfusion catheter tube can be held within acceptable boundaries. This means that for stenosis with narrow entry openings as frequent in cardiovascular angioplasty, instruments with exceptionally wide perfusion channels can be used. And as a result of the fact that, upon inflation of the balloon for dilatation, its inner wall is allowed to collapse onto the small tubular conduit, and upon inflation of the balloon for vessel wall support, the portion of its wall forming the perfusion tunnel for the perfusion catheter is kept open by the large diameter perfusion catheter, the balloon can have and extremely thin wall with no internal ribs, weldings or struts to achieve the lowest possible profile in deflated condition while withstanding the required pressures.

According to a preferred embodiment of the invention, the balloon forms a hollow cylinder without internal support for its walls and this balloon is closed by welding it inside wall to inside wall at its proximal end, so that the welding places of the balloon may also stay outside the stenosis. And within this frame, to get rid of any welding points and peak stresses at the distal end of the balloon, and thereby achieve the narrowest diameter at that place, the balloon may be linked to the tubular conduit by a net affixed to the distal end of the tubular conduit, which net extends all the way around and along the balloon to be welded to the proximal end thereof.

The invention will now be described more particularly with reference to the accompanying drawings which show, by way of example only, a preferred embodiment and variant of the invention.

BRIEF DESCRIPTION OF THE DRAWINGS

FIG. 1 is an axial section showing the components of the angioplasty perfusion catheter in a presentation configuration.

FIG. 2 shows separately the components of the angioplasty perfusion catheter of FIG. 1.

FIG. 3 is a transverse section along line I—I of FIG. 1.

FIGS. 4 to 8 are diagrammatic sections illustrating the operating steps of the angioplasty perfusion catheter.

FIG. 9 illustrates a detail of the angioplasty perfusion catheter.

FIG. 10 illustrates the variant.

DETAILED DESCRIPTION OF THE INVENTION

The angioplasty perfusion catheter shown in FIGS. 1 and 3 comprises five coaxial components, namely, a perfusion catheter 1;

a dilatation balloon 2 having a wall 3, which wall forms a torus elongated in the longitudinal direction of the perfusion catheter and defines a perfusion tunnel 4 adapted to allow passage of the perfusion catheter 1 when the balloon is deflated; this balloon which is independent from the perfusion catheter 1, forms a hollow cylinder without internal supports for its walls, and it is welded inside wall to inside wall at its proximal end 18, which may be achieved by the known shrink tube technology;

a guide wire 5 with preshaped tip 6 at its distal end which can have any shape appropriate to reaching a stenosis;

a tubular conduit 7 surrounding with play the guide wire 5; and a dilator member 8 sliding inside and along the perfusion catheter 1, such dilator member also sliding around and along the tubular conduit 7, and having a distal end with an outer wall in the shape of a tapering truncated cone 9.

The dilation balloon 2 is connected by its distal end to the distal end of the tubular conduit 7 by means of a movable apertured link, in the example shown, two diametrically opposed and oblique flexible straps 10; the balloon 2 is further connected at its proximal end to an inflating tube 11 connected to a supply of pressurized liquid (not shown).

The perfusion catheter 1 comprises on its wall a plurality of side orifices 12, the number of which may vary as a function of their size, located before the dilatation balloon 2 when the perfusion catheter is fully engaged within the perfusion tunnel 4 of the balloon. These orifices are for allowing blood flow through the catheter and up to a central outlet 13 thereof when the balloon is inflated in a stenosis, the perfusion catheter thus defining a perfusion channel 131.

The tubular conduit 7 also comprises on its wall a plurality of side orifices 14 arranged before, in the middle, and in front of the area covered by the balloon in order to allow blood flow within the conduit 7 when the guide wire 5 is withdrawn.

Referring now more particularly to FIGS. 4 to 8, FIG. 4 shows the first operating step in which the balloon 2 is deflated and inserted into a stenosis ST by means of the tubular conduit 7 directed by the guide wire 5 and dragging the balloon via the oblique straps 10, while the perfusion catheter 1 and dilator member 8 are left in waiting condition behind the stenosis. In this condition, the balloon 2 occupies a diametral space which is minimal and substantially smaller than the diameter of the perfusion catheter. The dilator member 8 has its truncated cone end 9 slightly outriding the distal end of the perfusion catheter 1.

The second step illustrated by FIG. 5 shows the guide wire 5, tubular conduit 7, perfusion catheter 1 and dilator member 8 in the same condition, the balloon 2 being inflated for a very short time at a pressure sufficient to break the stenosis in order to permit easy passage of the perfusion catheter 1. The balloon is then deflated to re-establish the blood flow within the enlarged stenosis.

Immediately after deflation of the balloon 2, and as shown in FIGS. 6 and 7, the operator slides the dilator member 8 and perfusion catheter 1 along the tubular conduit 7 of the guide wire 5 in order to make way into the perfusion tunnel 4 of the deflated balloon 2 by pushing therein the truncated cone end 9 of the dilator member 8; upon continuing to push the dilator member and perfusion catheter while holding back the balloon 2 by the inflating tube 11, the operator fully inserts the dilator member 8 and perfusion catheter 1 into the perfusion tunnel 4 of the balloon as shown in FIG. 7. At that stage, the distal end of the perfusion catheter slightly exceeds the distal end of the deflated balloon 2.

Turning now to the last step illustrated in FIG. 8, the dilator member 8 is pulled back past the side orifices 12 of the perfusion catheter 1 and the balloon 2 is inflated at a relatively low pressure to support the vessel wall. At that point, the balloon may remain inflated as long as needed because the blood flow through the stenosis is assured from the side orifices 12 up to the central outlet 13 through the perfusion channel 131 of the perfusion catheter 1.

In this last step, it is possible to increase the flow capacity of the blood within the perfusion channel 131 by withdrawing the guide wire 5 beyond the side orifices 14 of the tubular conduit 7 which are located before the area covered by the balloon 2. Upon doing so, an added quantity of blood can pass through the tubular conduit 7 and, as the wall of that tubular conduit may be quite thin, it is nearly the whole of the inner section of the perfusion channel 131 of the perfusion catheter that may be used for blood flowing purposes during inflation of the balloon.

In order to control the relative positions of the components of the angioplasty perfusion catheter during the various operating steps described hereabove, detecting means are provided for as exemplified on FIG. 9. As shown, there are four radio-opaque markers 15 and 16 and one non radio-opaque marker 17. In the operating position corresponding to the showing of FIG. 7, one radio-opaque marker 15 is located at the distal end of the tubular conduit 7, and three radio-opaque markers 16 are located facing each other respectively on the tubular conduit 7, on the dilator member 8 and at the junction of the inflating tube 11 with the balloon 2. The non radio-opaque marker 17 is located on the proximal portion of the dilator member 8, out of the body of the patient, at the place corresponding to the location of the proximal part of the perfusion catheter 1 in the operating position shown in FIG. 7. Of course, there may be other arrangements for the detecting means.

The number of side orifices 14 of the tubular conduit 7 may also vary depending on their size, being understood however that, in case of use of such orifices, there must be at least one orifice 14 behind the area covered by the balloon.

The balloon may be welded otherwise than inside wall to inside wall as described.

Depending on the respective dimensions of the various integers, the distal end of the dilator member may avoid the truncated shape shown; the angioplasty perfusion catheter may even be devised without the dilator member.

According to a preferred variant shown in FIG. 10, the distal end of the tubular conduit 7 is connected to the balloon 2 by means of a net 19, for instance tubular, affixed in the region of the distal end of the tubular conduit and extending all the way around and along the balloon 2 to be welded at the proximal end 18 thereof, in the example shown at the place of the face to face welding of the balloon. The strands extending from one end of the link to the other will contract the tubular net if brought under tension. Therefore, this net will contract under axial tension by the tubular conduit, keeping the deflated balloon closely applied against the tubular conduit, thereby achieving minimal diameter for insertion into the stenosis. This net may also be stretch, that is to say with a capacity for being distended or enlarged by force, to still enhance the applying of the balloon against the tubular conduit and minimise the profile at the distal end of the balloon.

I claim:

1. An angioplasty catheter system with a perfusion channel, comprising:

a dilatation balloon having proximal and distal ends with the proximal end being free, said balloon defining a perfusion tunnel extending therethrough between said proximal free end and said distal end;

inflation tube means connected to the balloon for inflation thereof; and perfusion catheter means for defining the perfusion channel, said perfusion catheter means extending proximally of the balloon for longitudinal movement through the proximal free end thereof and within the perfusion tunnel.

2. A catheter system according to claim 1, further comprising a tubular conduit defining a guide wire lumen, said tubular conduit having proximal and distal ends and said tubular conduit extending through the perfusion tunnel of the balloon.

3. A catheter system according to claim 2, wherein said perfusion catheter means is surrounding the tubular conduit.

4. A catheter system according to claim 2, wherein the balloon is connected to the tubular conduit by an apertured flexible link.

5. A catheter system according to claim 4, wherein said apertured flexible link is connected to said distal end of the balloon.

6. A catheter system according to claim 2, further comprising flexible net means affixed to the distal end of said tubular conduit, said net means extending around and along the balloon and said net being affixed to said proximal free end of the balloon.

7. A catheter system according to claim 6, wherein said net means is tubular.

8. A catheter system according to claim 7, wherein said net means has a capacity for being enlarged by force.

9. A catheter system according to claim 2, wherein said tubular conduit has at least one side orifice in fluid communication with the guide wire lumen along a proximal portion thereof.

10. A catheter system according to claim 1, wherein said balloon forms a hollow cylinder defining an inside wall and an outside wall without internal support for the inside wall and the outside wall, and wherein said balloon is closed by welding the inside wall to the inside wall at said proximal free end of the balloon.

11. A catheter system according to claim 1, further comprising a dilator member movably disposed inside the perfusion catheter means.

12. A catheter system according to claim 11, wherein said dilator member has a distal end with an outer wall in the shape of a truncated cone.

13. A catheter system according to claim 1, further comprising a tubular conduit defining a guide wire lumen said tubular conduit having proximal and distal ends and said tubular conduit extending through the perfusion tunnel of the balloon, a dilator member movably disposed inside the perfusion catheter means, and means for detecting the relative position of the tubular conduit and of the dilator member with respect to the perfusion catheter means and to the balloon.

* * * * *